United States Patent
Hiltunen et al.

(10) Patent No.: US 10,087,477 B2
(45) Date of Patent: Oct. 2, 2018

(54) PROCESS FOR PRODUCING FIBRILLATED CELLULOSE MATERIAL

(71) Applicant: Teknologian tutkimuskeskus VTT Oy, Espoo (FI)

(72) Inventors: Jaakko Hiltunen, Espoo (FI); Katariina Kemppainen, Espoo (FI); Jaakko Pere, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 0 days.

(21) Appl. No.: 15/104,991

(22) PCT Filed: Dec. 18, 2014

(86) PCT No.: PCT/FI2014/051023
§ 371 (c)(1),
(2) Date: Jun. 16, 2016

(87) PCT Pub. No.: WO2015/092146
PCT Pub. Date: Jun. 25, 2015

(65) Prior Publication Data
US 2016/0355857 A1 Dec. 8, 2016

(30) Foreign Application Priority Data

Dec. 18, 2013 (FI) ........................... 20136282

(51) Int. Cl.
| | |
|---|---|
| *C12P 19/14* | (2006.01) |
| *C12P 19/04* | (2006.01) |
| *D21C 5/00* | (2006.01) |
| *C08B 15/02* | (2006.01) |
| *C08L 1/04* | (2006.01) |
| *D21H 11/18* | (2006.01) |

(52) U.S. Cl.
CPC ............ *C12P 19/14* (2013.01); *C08B 15/02* (2013.01); *C08L 1/04* (2013.01); *C12P 19/04* (2013.01); *D21C 5/005* (2013.01); *D21H 11/18* (2013.01)

(58) Field of Classification Search
None
See application file for complete search history.

(56) References Cited

U.S. PATENT DOCUMENTS

| | | | |
|---|---|---|---|
| 8,747,612 B2 | 6/2014 | Heiskanen et al. | |
| 2012/0187226 A1* | 7/2012 | Tarverdi | D21B 1/12 241/21 |
| 2012/0316330 A1* | 12/2012 | Zhu | B82Y 40/00 536/56 |

FOREIGN PATENT DOCUMENTS

| | | |
|---|---|---|
| CN | 102472014 A1 | 5/2012 |
| EP | 2853635 A1 | 4/2015 |
| JP | 2012533000 A | 12/2012 |
| WO | WO9420666 A1 | 9/1994 |
| WO | WO9628606 A1 | 9/1996 |
| WO | WO9856981 A1 | 12/1998 |
| WO | WO2004055268 A1 | 7/2004 |
| WO | WO2005056915 A1 | 6/2005 |
| WO | WO2011004284 A1 | 1/2011 |
| WO | WO2011004301 A1 | 1/2011 |
| WO | WO2011051882 A1 | 5/2011 |
| WO | WO2013176033 A1 | 11/2013 |
| WO | WO2015150620 A1 | 10/2015 |
| WO | WO2016071573 A1 | 5/2016 |

OTHER PUBLICATIONS

Pääkkö M. et al: Enzymatic hydrolysis combined with mechanical shearing and high-pressure homogenization for nanoscale cellulose fibrils and strong gels. Biomacromolecules, Jan. 2007, vol. 8, s. 1934-1941.
Suchy M. et al: Effects of commercial cellobiohydrolase treatment on fiber strength and morphology of bleached hardwood pulp. Holzforschung, 2009. vol. 63, No. 6, lines 731-736.

\* cited by examiner

*Primary Examiner* — Michelle F. Paguio Frising
(74) *Attorney, Agent, or Firm* — Seppo Laine Oy

(57) ABSTRACT

The present invention relates to a process for producing a fibrillated cellulose material. In the invention fibrillated cellulose is produced enzymatically by using a low energy demanding mechanical mixer such as plough share mixer, to enhance the fibrillation. Enzymes and process conditions are chosen so that the cellulose degradation is as low as possible, while obtaining a high yield of nanofibrils. Sugars that are produced into the end-product may also be furthermore exploited.

13 Claims, 4 Drawing Sheets

PROCESS FOR PRODUCING FIBRILLATED CELLULOSE MATERIAL

FIELD OF THE INVENTION

The present invention relates to a process according to preamble of claim 1 for producing fibrillated cellulose material, and to a fibrillated cellulose according to claim 11.

DESCRIPTION OF RELATED ART

Cellulose is a polysaccharide derived from D-glucose units, which condense through β (1→4)-glycosidic bonds. It can comprise several hundred to over ten thousand glucose units. Cellulose is a straight chain polymer and the molecule adopts an extended rod-like conformation, aided by the equatorial conformation of the glucose residues. Cellulose is also the most common organic compound on earth and it is the structural component of the primary cell wall of green plants.

Nanocellulose, also known as nanofibrillated cellulose (NFC) or microfibrillated cellulose (MFC) is a material composed of nanosized cellulose fibres. Nanocellulose fibre is very thin, having the width of 5-20 nm. Longitudinal dimension can vary widely, and it may be from 10s of nanometers to several microns. Nanocellulose can be prepared from any cellulose material, but wood pulp is often used.

There are many research and development projects ongoing in the area of nanocellulose production. Normally, the production of nanocellulose fibres from wood material requires mechanical treatment, like grinding or high-pressure homogenizing characterized with high energy consumption. Pre-treatments such as strong acid hydrolysis, oxidation, chemical functionalization and enzymatic treatments, or their combination are also studied.

The problem with chemical oxidation and enzymatic hydrolysis is that these usually cause unwanted degradation of cellulose polymers resulting to decrease of cellulose DP (degree of polymerization) and thus to fibrils of undesirable quality and, on the other hand release of soluble sugars. Although the production process is rather expensive and difficult to control, the properties of nanocellulose (e.g. mechanical, film-forming and viscosity properties) makes it an interesting material for many application fields, such as paper, composite, food, medical and cosmetic industries, to mention few.

Nanocellulose can also be produced by using bacteria. Bacterial nanocellulose is prepared via a biosynthetic process and it is attracting a lot of interest in the research field. Future applications can be found for example around the biomedical area. These processes are, however, time consuming and expensive to implement.

FI 122776 B1 describes a process for producing relatively pure nanocellulose in an industrial scale and a nanocellulose product thereof. The invention provides a solution for nanocellulose production with ⅓ of the energy consumption compared to prior art. In the example of the publication, a process is described, which comprises two grinding steps and a few additional steps (e.g. precipitation). The feed slurry consistency is however rather low (3%), and the process itself differs highly from the process of the present invention.

WO 2011/004284 A1 describes a process for the production of microfibrillated cellulose, from wood pulp, in an improved and energy efficient process. In the example of the publication, pine kraft pulp is used as a starting material and an enzyme treatment is carried out with an endoglucanase-rich enzyme preparation. From the results can be concluded, that a process comprising combined simultaneous mechanical and enzymatic treatment is more efficient compared to a process, in which these steps are carried out sequentially. The process described in the corresponding U.S. Pat. No. 8,747,612 requires however addition of at least one modifying chemical, more precisely an oxidative chemical such as hydrogen peroxide, which results a reaction between the fiber and the chemical.

However, there is still a need for energy efficient processes, by which controlled and minimized cellulose degradation and therefore better end-product yields and desired fibril size are achievable.

SUMMARY OF THE INVENTION

It is an object of the present invention to provide an improved process for production of fibrillated cellulose. Particularly, it is an object of the present invention to provide an energy-efficient production process with better end-product yield, quality and higher end-product dry matter content.

These and other objects, together with the advantages thereof over known process and processes, are achieved by the present invention, as hereinafter described and claimed.

The present invention is based on the ability of certain cellulases to loosen and fibrillate cellulose structure and use of a tailored enzyme mix, which facilitates fibrillating activity instead of cellulose hydrolysis. According to the present invention, the desired fibrillated cellulose is produced by using the enzyme mix, which comprises mainly cellobiohydrolase(s), some endoglucanase(s), and may also contain other enzyme activities, such as β-glucosidase or hemicellulases.

These enzymes are preferably used in a ratio, which minimizes the cellulose degradation, but accelerates production of fibrillated cellulose. This type of action is favored by choosing enzymes with varying thermostability and controlling their activity by process temperature. The loosening of the cellulose fibres is achieved preferably by simultaneous enzymatic and mechanical treatment.

More specifically, the process of the present invention is characterized by what is stated in the characterizing part of claim 1.

Further, the fibrillated cellulose produced according to the invention is characterized by what is stated in claim 11.

Considerable advantages are obtained by the means of the invention. For example, the present invention provides an energy efficient process for producing fibrillated cellulose, better product yields at high solids content. Furthermore the process of this invention can be carried out with less enzyme addition than described in prior art. Optionally, also secondary products (monosugars) that are produced within this process can be further utilized, thus making the total process more profitable and industrially attractive.

Another advantage of the present invention is that the enzyme treatment is gentler towards cellulose fibres compared to prior solutions. By controlling process conditions, i.e. temperature, treatment time and mixing, product quality in terms of degree of fibrillation and polydispersity index can be tuned according to the needs of different end-use applications.

Another further advantage is that the product after treatment has lower moisture content (60-80%) compared to existing methods producing nanocellulose at 97-99% moisture content. Thus, the material can be applied to processes which cannot tolerate large amounts of water associated with the fibrillated cellulose.

Next, the invention will be described more closely with reference to the attached drawings and a detailed description.

DESCRIPTION OF THE DRAWINGS

FIG. 2 shows a material after 4 h (2a) and 20 h (2b) treated with Ecopulp Energy (cellobiohydrolase) and FIG. 3 shows material after 2 h (3a) and 20 h (3b) treated with Novozym 476 (endoglucanase).

DETAILED DESCRIPTION OF THE PREFERRED EMBODIMENTS OF THE INVENTION

The present invention relates to a process for producing fibrillated cellulose in an improved and energy efficient way, which process comprises a fibrillation of the starting cellulose material with enzyme(s) and enhancing the fibrillation mechanically.

Figure 1:
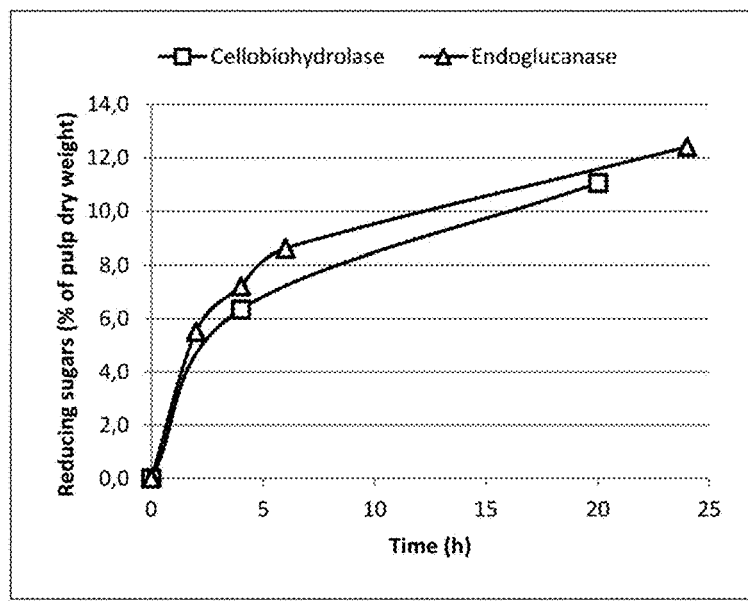
FIG. 1 is a chart showing the release of reducing sugars during the treatment. Endoglucanase treatment produces more reducing sugars with a lower enzyme dosage causing more yield loss of the pulp.
Figure 2A:
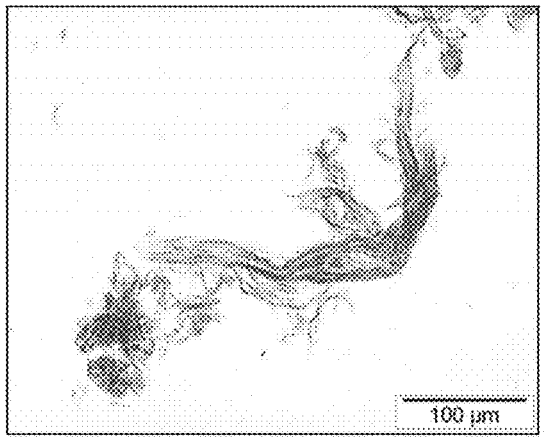
FIGS. 2 and 3 present microscopy images from two treatments. Cellobiohydrolase fibrillates fibre surface and fibre ends producing fine long fibre pieces, whereas endoglucanase has more cutting effect and produces standardized short fibre pieces.
Figure 2B:
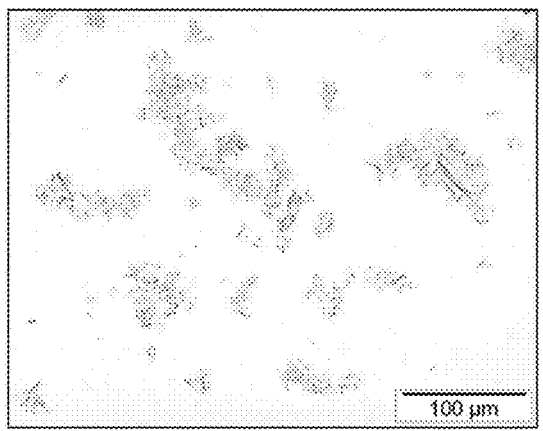
Figure 3A:
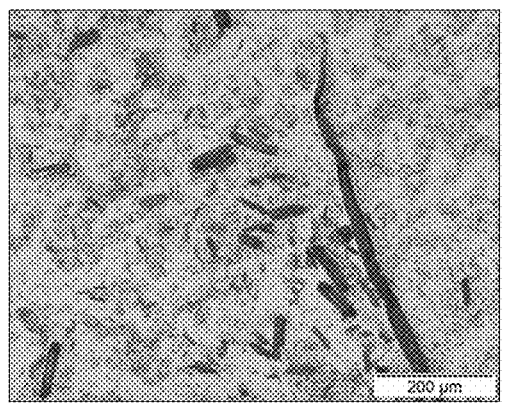
Figure 3B:
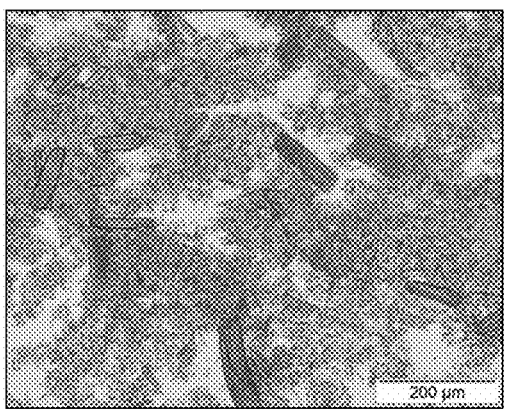
Figure 4:
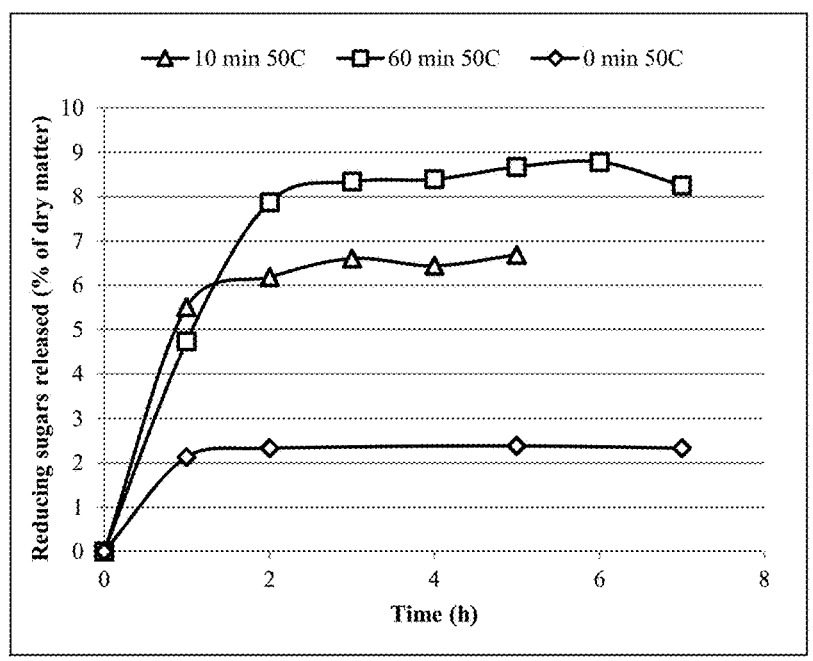
FIG. 4 is a chart showing the release of reducing sugars during a treatment. The lower temperature in the beginning allows the main (cellobiohydrolase) and the side activity (endoglucanase) to function synergistically resulting to formation of new chain ends for attack of CBHs. When temperature is increased, only cellobiohydrolase is able to function resulting to level-off of sugar production due to closing down synergistic cellulose hydrolysis. The treatment is carried out at 70° C., except in the beginning the temperature was held at 50° C. for 0, 10 or 60 min.
Figure 5A:
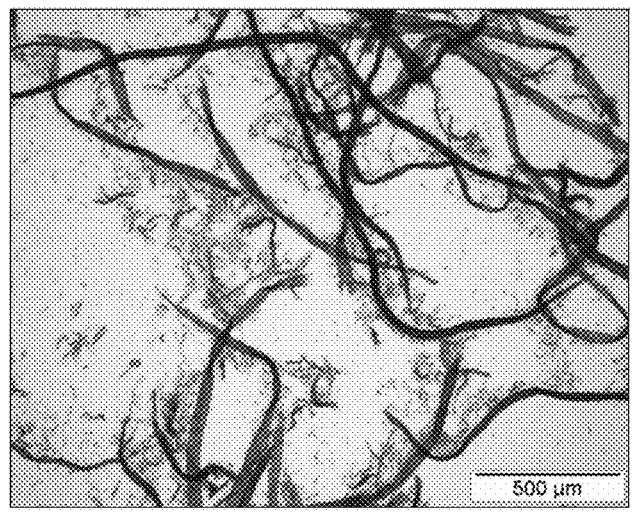
FIG. 5a shows a material treated with Ecopulp Energy at 70° C. for 7 h, FIG. 5b at 50° C. for 10 min and 4 h 50 min at 70° C.
Figure 5B:
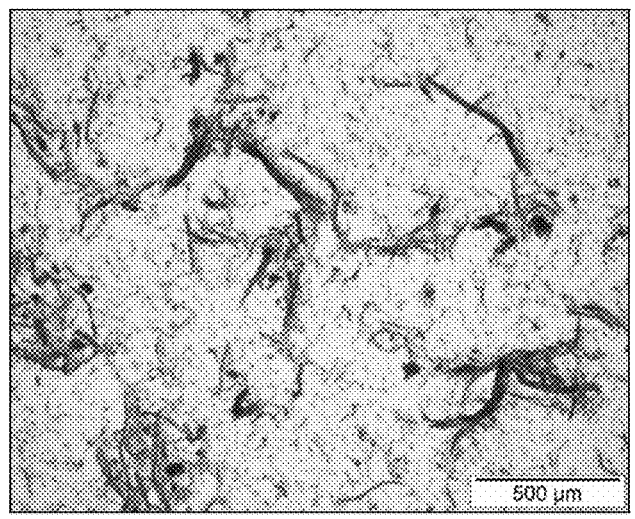
FIG. 5 presents microscopy images of the materials with treatment at varying temperature profiles. The treatment at 70° C. preserves fibres long and only a small amount of fibrillation takes place. When temperature is kept at 50° C. for 10 min in the beginning of the treatment more fibrillation takes place and there are less intact fibres after treatment. Keeping the temperature at 50° C. for 1 h further increases the degree of fibrillation.
FIG. 5c at 50° C. for 60 min and 4 h at 70° C.
Figure 5C:
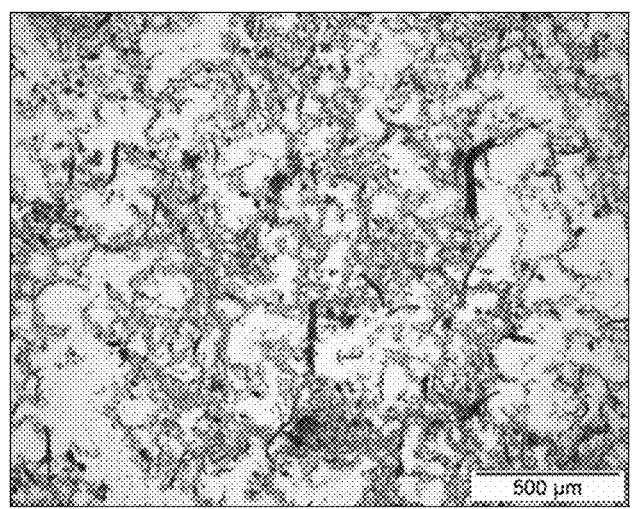

The term "fibrillated cellulose" is here intended to encompass all fibrillated cellulose materials, having in minimum lateral dimensions of 5-20 nanometers and longitudinal dimensions from 10 nanometers to several microns, even up to 100 µm. Fiber distributions however typically contain also longer fibers, such as around 500 µm as shown e.g. in FIGS. 5b and 5c. Thus, also materials traditionally named "microfibrillated cellulose" are included in the scope of the present invention.

As a starting material pulp, unbleached pulp or native biomass of different origin (e.g. wood, annual plants, crop residues) can be used. Pulp material can be for example bleached pine pulp. Particularly, "slurry" is used, which is here intended to mean a starting material, e.g. wood pulp, which comprises the cellulose fibres that are processed in an aqueous dispersion. The starting consistency of the slurry (i.e. weight-% of the cellulose matter in the aqueous dispersion) is preferably higher than 10% and more preferably higher than 15% by weight of the total slurry. Slurry consistency may be even over 30%. The starting material i.e. pulp or biomass can also be in a grinded form.

According to one embodiment the starting slurry consistency is between 10% and 60%, preferably between 15% and 40%.

In prior art technology fibrillation is generally carried out by grinding or high-pressure homogenizing, possibly with the help of chemical pre-treatments such as strong acid hydrolysis or chemical oxidation. A preferred option according to the present invention is to use an enzymatic fibrillation in conjunction with low energy mixing, i.e. a procedure including at least one enzymatic treatment of the fibres. Suitable machinery includes any equipment enabling adequate mixing in high consistency without having an excessive high shear or cutting action upon fibres. These include e.g. mixers, compounders, extruders or kneaders. This enzymatic fibrillation can be enhanced by using a mechanical treatment to further disintegrate the fibres, which mechanical treatment for example can be carried out by using a homogenizer, a grinder or a fluidizer.

Said combination of mechanical treatment and enzymatic treatment results in a much more efficient production process for fibrillated cellulose compared to the simultaneous procedure used in the prior art. The increased efficiency is due to the synergistic effect of this combined treatment. The mechanical treatment carried out in high consistency conditions in conjunction with the enzymatic treatment will open and unravel fibre cell wall allowing the enzymes to have easier access to the fibre matrix. Enzymes will then attack to uncovered fibre surfaces and further disintegrate fibre structure. Because of the combined treatment, the enzymes are distributed more thoroughly and homogeneously throughout the slurry and they will find more suitable places to attach to, thus making the fibrillation more efficient. High consistency promotes gentle fibre-fibre friction which enhances the fibrillating effect of the treatment. Since the enzymatic treatment loosens up the fibres, mechanical treatment can be performed in a softer manner and in milder reaction conditions.

An advantage of this invention is that fibrillated cellulose is produced enzymatically, i.e. gently, by using a low energy demanding mechanical mixer. Another advantage is that it is possible to enhance the fibrillation in a desired and controlled way, without too high degradation, thus producing fibrillated material of a controlled quality. Enzymes are used so that the cellulose degradation compared to the produced fibrillated material is as low as possible. Sugars that are produced into the end-product may also be furthermore exploited. Researchers have shown that these sugars can be fermented to for example ethanol by common yeast.

In prior art the enzymatic treatment of cellulose is performed with an enzyme mix comprising at least three of the following: cellulose, hemicellulose, or their hydrolysis products degrading proteins, including endoglucanases, cellobiohydrolases, mannanases, xylanases and β-glucosidases. The present invention, however, is characterized in that the fibrillation is carried out by using an enzyme mix having mainly a cellobiohydrolase (CBH) activity and a low endoglucanase (EG) activity, wherein the endoglucanase activity is very low, but sufficient enough to create new chain ends for CBH action. In addition, it is preferred to use an enzyme mix and reaction conditions, wherein the cellobiohydrolase activity is more thermostable than the endoglucanase activity. The enzyme mix may optionally contain fibrillation assisting carbohydrate active enzymes such as β-glucosidases, hemicellulases, pectinases or lytic polysaccharide mono-oxygenases (i.e. LPMOs, which are capable of oxidizing and thus cleaving recalcitrant polysaccharides), or their combinations.

Cellobiohydrolases (CBHs) have been shown to act processively and unidirectionally along cellulose fibre starting either from reducing or non-reducing chain end and liberating cellobiose as the main product. Characteristic for CBHs are that DP (degree of polymerization) of cellulose is affected only slightly. Endoglucanases attack randomly along cellulose chain creating new sites for CBHs to act. The extent of new chain ends created by endoglucanases can be controlled by enzyme dosage, treatment time and temperature profile or their combinations. The role of β-glucosidase is to hydrolyze arising cello-oligomers to glucose and to prevent end-product inhibition of CBHs.

An important improvement in the present invention is that the different thermostability of the enzymes allows their selective inactivation by controlling process temperature. Thus, the production of sugars is kept to a minimum and the degree of hydrolysis remains low. Secondly, precise control of endoglucanase activity during treatment enables production of variable grades of fibrillated material, e.g. in terms of cellulose DP.

The reaction temperature of the process is chosen according to the enzymes that are used. In one preferred embodiment the fibrillation is carried out in two stages: selecting such reaction temperature, which allows both cellobiohydrolase and endoglucanase to be active in a first stage and inactivating the endoglucanase activity by increasing the reaction temperature in a second stage. Thereby, it is preferred to use temperatures between 0 and 50° C. in the first stage and temperatures between 60 and 80° C. in the second stage. After treatment, when necessary, inactivation of enzyme activity can be performed by heating up the material to 100° C. for 15-30 min e.g. by steam. Alternatively, inactivation can also be carried out by pH adjustment outside pH optima of the enzymes.

In one preferred embodiment the temperature is kept low (below or about 50° C.) in the beginning of the reaction and then raised to about 70° C. for the remaining reaction time.

Enzyme products usually always contain minor traces of side activities. Herein low temperature first allows the enzymes to co-operate, after which high temperature inactivates the remaining side activities allowing cellobiohydrolase work alone on the fibre.

Based on the above described temperature and/or pH controlling, in one embodiment the reaction is carried out by having only endoglucanase activity in a first stage and only cellobiohydrolase activity in a second stage (i.e. CBH addition and EG inactivation in a second stage) or by using an enzyme mix comprising said enzymes with high initial endoglucanase activity, which is correspondingly inactivated e.g. by increasing the temperature in a second stage.

CBH I and CBH II tend to hydrolyze cellulose from chain ends, whereas endoglucanase attacks randomly cellulose chain with concomitant decrease of DP. It is thereby preferred to use an enzyme mix, which has at least small traces of endoglucanase activity, because cellobiohydrolases can utilize chain ends that are provided by endoglucanase. Sufficient amount of endoglucanase is dependent on endoglucanase in question, since specific activity of endoglucanases varies greatly and some of them are very difficult to analyze even with the most sensitive methods (e.g. CMC viscosity method). Therefore proper amount of endoglucanase activity can even exist as a contaminant side activity in the preparation. Higher endoglucanase activities, however, work synergistically with CBH releasing a lot of soluble oligo-saccharides causing yield losses.

The treatment time can vary between 15 minutes and 25 hours, but preferably from 1 hour to 6 hours. Enzymes are added before or during the mechanical treatment, for example by spraying. It is noteworthy, that by using enzymes and low energy demanding mechanical mixing together, also longer treatments lead to a more energy efficient process, compared to traditional processing, such as grinding and high-pressure homogenizing.

According to one preferred embodiment, mechanical agitation is carried out without using grinding forces that cause excessive degradation of the fibres and consumption of energy. An example of a suitable non-grinding and low energy demanding mechanical mixer to be used in the process of the present invention is a non-refining mixer thus exerting grinding forces, such as a plough share mixer, a screw mixer, a kneader, a compounder or an extruder. Mixing speed should be kept rather low, preferably around 100 rpm. In addition, according to a further embodiment, the fibrillation may be enhanced by a post-treatment step such as a grinding or a high shear treatment in an extruder, a homogenizer or a fluidizer.

According to another embodiment the product i.e. fibrillated cellulose material after above described treatments has lower moisture content (60-80%) compared to existing methods producing nanocellulose at 97-99% moisture content. Thus, the material can be applied to processes which cannot tolerate large amounts of water associated with the fibrillated cellulose.

The soluble oligo-saccharides can be further hydrolyzed to form monosugars as the secondary end-product, which can be exploited even further in optional subsequent yeast or bacteria fermentation for production of chemicals. The possible fermentation step also purifies the end-product.

The present invention can be further applied e.g. in the production of sugar-based chemicals for industrial needs, preferably while utilizing also the production of fibrillated cellulose, or the invention can be further applied in the production of composites, paper and cardboard products, films and food products. The process is industrially feasible, does not need unreasonable equipment investments and fits perfectly to the strategy of future biorefineries.

Herein below the present invention is illustrated by non-limiting examples. It should be understood, however, that the embodiments given in the description above and in the examples are for illustrative purposes only, and that various changes and modifications are possible within the scope of the claims.

Example 1

In the experiment the effect of cellobiohydrolase (8 mg/g Ecopulp Energy, AB Enzymes) and endoglucanase (5 mg/g Novozym 476, Novozymes) enzymes products on bleached softwood kraft pulp was compared. Enzymes were dosed as mg protein per g dry fibre. In both experiments 1 mg/g betaglucosidase enzyme product (Novozym 188, Novozymes was added). The treatment was carried out at 25% consistency in a 5 L reactor with a ploughshare mixing element (DVT5, Lödige). Mixing rate was 100 rpm and temperature 50° C.

Table 1 presents the properties of the enzymatically treated materials. A sample treated only mechanically without enzymes is shown for reference. CBH treatment reduced crystallinity and produced material with less fibres and fines compared to EG treatment showing that more material was degraded into particles smaller than the fibres and fines analysed by the apparatus. The table also shows the endoglucanase activity dosed to the system per gram of fibre. The endoglucanase activity was measured using hydroxyethyl cellulose as the substrate (HEC activity).

TABLE 1

Properties of the enzymatically treated materials.

| Property | No enzymes 24 h | CBH 4 h | CBH 20 h | EG 6 h |
|---|---|---|---|---|
| HEC activity dosed (nkat/g fibre) | 0 | 36 | | 969 |
| Viscosity | 880 | 360 | 170 | 300 |
| Crystallinity (%) | 54 ± 3 | 54 ± 3 | 51.3 | 57 ± 3 |
| Molar mass weight average (Da) | 132 300 | 31 300 | 14 800 | 33 800 |
| Molar mass number average (Da) | 930 600 | 313 800 | 163 800 | 246 100 |
| Polydispersity of molar mass | 7 | 10 | 11.1 | 7.3 |
| Fibre content (/mg) | n.a. | 21 538 | 10 111 | 49 604 |
| Fines content (%) | n.a. | 72 | 84.8 | 99 | n.a. = not analysed

Example 2

In the experiment different temperature profiles were used to control the side activities and the fibrillation of the pulp. Cellobiohydrolase product (8 mg/g Ecopulp Energy, AB Enzymes) was used, which contains mainly thermostable cellobiohydrolase and minor amounts of less thermally stable endoglucanase as a side activity. Less thermostable betaglucosidase (1 mg/g Novozym 188) was also added. The treatment was carried out for bleached softwood kraft pulp at 25% consistency in a Hobart pulper. At first the temperature was adjusted to 50° C. for 0, 10 or 60 min and then increased to 70° C. to inactivate the less thermostable side activities.

While the above description and examples show and describe and point out fundamental novel features of the invention as applied to a preferred embodiment thereof, it will be understood that various omissions and substitutions and changes in the details of the process and products may be made by those skilled in the art without departing from the spirit of the invention. For example, it is expressly intended that all combinations of those elements and/or process steps which perform substantially the same operations or give substantially the same results as those achieved above are within the scope of the invention. Substitutions of the elements from one described embodiment to another are also fully intended and contemplated. It is also to be understood that the drawings are not necessarily drawn to scale but they are merely conceptual in nature. It is the intention, therefore, to be limited only as indicated by the scope of the claims appended hereto.

Example 3

The enzymatic treatment on bleached softwood kraft pulp was performed as described in Example 2 except that mixing was carried out in a sigma mixer (Farinograph, Brabender Gmbh). The enzyme dosage was 8 mg/g (EcoPulp Energy, AB Enzymes) and the pulp consistency 25%. The temperature was first set to 50° C. for 1 hour and thereafter increased to 70° C. for 8 hours. After the treatment enzyme activity was stopped by boiling the pulp at 100° C. for 15 min. The pulp was thoroughly washed with distilled water.

Preparation of the fibrillated cellulose for SEM imaging was carried out as follows: Nanocellulose sample was diluted with water to approx 0.1%, volume ~100 ml. The sample was then homogenized with UltraTurrax. 10 ml of diluted sample was taken, and further diluted to total volume of 20 ml (no homogenization) and filtrated in a Millipore glass funnel onto Durapore 0.45 µm HVLP04700 membrane. Directly after filtration, the filter membrane is inserted into 100% ethanol for at least 2×30 min. Membranes with NFC films are dried between two dry filter papers in oven at 55° C. at least overnight. The sample was imaged with LEO DSM 982 Gemini FEG-SEM at low electron energies.

The sample was prepared for AFM imaging as follows: a dilute suspension of the fibrillated cellulose was dried on freshly cleaved mica. Topography images of the sample was captured with an atomic force microscope (NanoScope IIIa Multimode AFM). A NanoScopeV Multimode8 AFM (E scanner, Bruker) and ScanAsyst-Air cantilevers (Bruker, f0=50-90 kHz, k=0.4 N/m) were used. All images were recorded in the ScanAsyst mode in air with scan rate 1 Hz. Images were only flattened to remove possible tilt in the image data, and no further processing was done.

Figure 6:
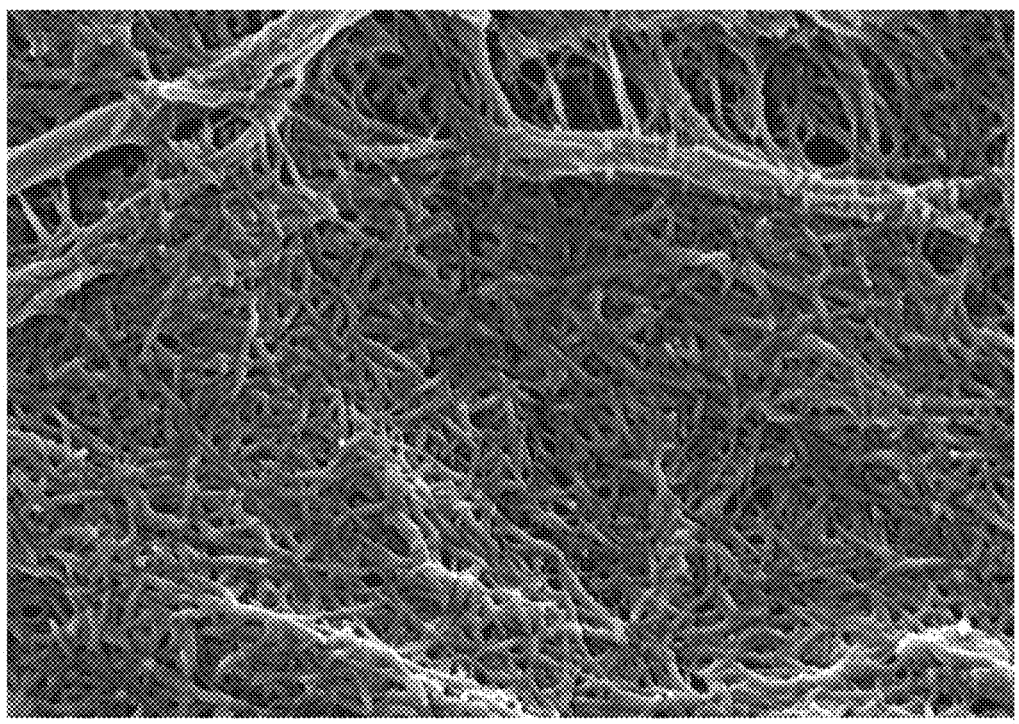
FIG. 6 is a SEM-image and FIG. 7 is an AFM-image showing the size of nanofibrillated cellulose produced by the process as hereinafter described.
Figure 7:
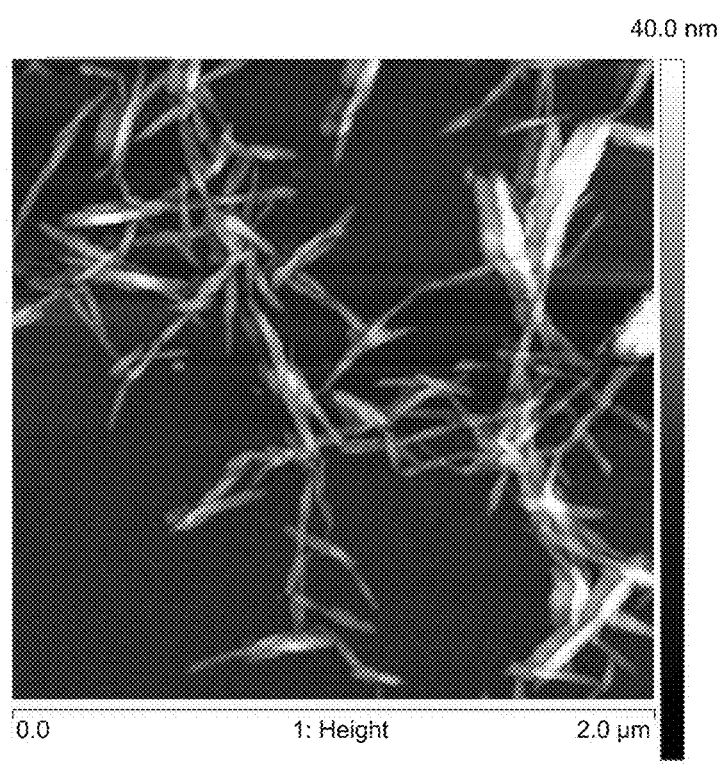

According to the SEM and AFM images (FIGS. 6 and 7) following conclusions can be made:
SEM: The fibrillated cellulose material was very homogenous with few larger fibril aggregates (fibril aggregate width 100-200 nm). Average lateral width of an individual fibril was 20 nm.
Based on AFM imaging approximate dimensions for individual fibrils were: width 15-20 nm, height 4-6 nm and length 100-400 nm.

CITATION LIST

Patent Literature

1. FI 122776 B1
2. WO 2011/004284 A1 (or U.S. Pat. No. 8,747,612 B2)

The invention claimed is:
1. A process for the production of fibrillated cellulose material comprising fibrillating a cellulose-based starting material with enzyme(s), and enhancing the fibrillating step with mechanical mixing, wherein before the fibrillating step a starting material is added into a slurry having a consistency of between 10% and 60%, after which the fibrillating step is carried out by using an enzyme mix having a main cellobiohydrolase activity and a side endoglucanase activity, wherein the endoglucanase activity is sufficient to create new chain ends, and wherein the cellobiohydrolase activity is more thermostable than the endoglucanase activity, combined with non-grinding mechanical mixing.

2. The process according to claim 1, wherein the fibrillating step is carried out in two stages by selectively controlling reaction temperature, comprising a first stage of selecting such reaction temperature, which allows both cellobiohydrolase and endoglucanase to be active, and a second stage, of inactivating the endoglucanase activity by increasing the reaction temperature.

3. The process according to claim 1, wherein the enzyme mix additionally contains assisting carbohydrate active enzymes such as β-glucosidases, hemicellulases, pectinases or lytic polysaccharide mono-oxygenases, or their combinations.

4. The process according to claim 1, wherein the mechanical mixing is carried out by using a low energy demanding mixer.

5. The process according to claim 4, wherein the low energy demanding mixer is a non-refining mixer exerting grinding forces.

6. The process according to claim 4, wherein the low energy demanding mixer is on of: a plough share mixer, screw mixer, kneader, compounder or extruder.

7. The process according to claim 1, wherein the fibrillating step is enhanced by a post-treatment step at adequate consistency.

8. The process according to claim 7, wherein the post-treatment step is grinding or high shear treatment in one of an extruder, homogenizer or fluidizer.

9. The process according to claim 1, wherein the fibrillating step is carried out in two stages, wherein in a first stage reaction temperature is maintained between 0 and 50° C. and in a second stage between 60 and 80° C.

10. The process according to claim 1, wherein the fibrillating step is carried out in two stages, wherein in a first stage reaction temperature is kept at about 50° C., followed by a second stage wherein the temperature is raised to about 70° C.

11. The process according to claim 1, wherein before the fibrillating step a starting material is added into a slurry having a consistency of between 15% and 40%.

12. The process according to claim 1, wherein the fibrillating step lasts from 15 minutes to 25 hours.

13. The process according to claim 1, wherein the fibrillation lasts from 1 hour to 6 hours.

* * * * *